United States Patent
Sixt

(10) Patent No.: US 8,151,599 B2
(45) Date of Patent: Apr. 10, 2012

(54) TRANSPORT CONTAINER FOR MAINTAINING THE TEMPERATURE OF FROZEN GOODS

(76) Inventor: Bernhard Sixt, Oberpframmern (DE)

( * ) Notice: Subject to any disclaimer, the term of this patent is extended or adjusted under 35 U.S.C. 154(b) by 754 days.

(21) Appl. No.: 12/373,347

(22) PCT Filed: Jul. 11, 2007

(86) PCT No.: PCT/EP2007/006138
§ 371 (c)(1),
(2), (4) Date: Jan. 12, 2009

(87) PCT Pub. No.: WO2008/006558
PCT Pub. Date: Jan. 17, 2008

(65) Prior Publication Data
US 2010/0000250 A1    Jan. 7, 2010

(30) Foreign Application Priority Data

Jul. 13, 2006  (DE) .......................... 10 2006 032 435

(51) Int. Cl.
*F25D 3/08* (2006.01)
(52) U.S. Cl. ...................... 62/457.2; 62/457.9
(58) Field of Classification Search ............ 62/457.1, 62/457.2, 457.3, 457.9, 371, 372, 268, 465, 62/530; 220/592.2, 592.27
See application file for complete search history.

(56) References Cited

U.S. PATENT DOCUMENTS

| | | | |
|---|---|---|---|
| 4,134,276 A * | 1/1979 | Lampard ......................... | 62/383 |
| 4,530,816 A | 7/1985 | Douglas-Hamilton | |
| 4,756,407 A * | 7/1988 | Larsen ............................. | 206/37 |
| 5,035,122 A * | 7/1991 | Oogjen ......................... | 62/457.2 |
| 5,103,651 A * | 4/1992 | Coelho et al. .................. | 62/341 |
| 5,355,684 A | 10/1994 | Guice | |
| 5,738,921 A * | 4/1998 | Andersen et al. ............ | 428/36.4 |
| 6,119,465 A * | 9/2000 | Mullens et al. ................... | 62/60 |
| 6,220,311 B1 * | 4/2001 | Litto .............................. | 141/67 |
| 6,226,997 B1 | 5/2001 | Vago | |
| 6,337,052 B1 | 1/2002 | Rosenwasser | |

(Continued)

FOREIGN PATENT DOCUMENTS

DE    198 30 551    1/2000

(Continued)

*Primary Examiner* — Mohammad Ali
(74) *Attorney, Agent, or Firm* — Michael J. Striker

(57) ABSTRACT

The invention relates to a transport container (1) comprising a superinsulation in the form of an evacuated insulating container (2) comprising a vacuum maintaining material (55). The transport container is provided with a cooling container (16) comprising a heat-conducting metal wool filling (57) and an organic coolant which undergoes a solid/liquid phase change in the temperature range of between −30° C. and −850° C. and has a heat of fusion of at least 50 J/ml. A slim cylindrical sample chamber (24) is used to receive deep-frozen tissue samples (26), said chamber being surrounded by the cooling container (16) and merging into a long neck opening (25) forming a single component therewith, said opening being largely filled by the insulating shaft (30) of a screwable plug (28) and sealed from the sample chamber (24). The air in the ring gap (32) created can be evacuated by means of an evacuating system (48). The plug (28) is provided with a stopper (38) protruding into the sample chamber (24) and a data logger (41) for recording the temperature in the sample chamber (24). Following the freezing of the coolant, the transport container (1) enables distribution times and intermediate storage of up to 14 days without any risk of damage to the tissue samples (26) received therein.

23 Claims, 13 Drawing Sheets

U.S. PATENT DOCUMENTS

| | | | |
|---|---|---|---|
| 6,673,594 B1 * | 1/2004 | Owen et al. | 435/284.1 |
| 6,968,711 B2 * | 11/2005 | Smith et al. | 62/371 |
| 7,004,655 B2 * | 2/2006 | Ferrara | 401/6 |
| 7,143,722 B2 * | 12/2006 | Ross | 123/3 |
| 7,959,369 B2 * | 6/2011 | Gueret | 401/123 |
| 2002/0190867 A1 | 12/2002 | Sommer et al. | |
| 2004/0136769 A1 * | 7/2004 | Ferrara | 401/6 |
| 2004/0231346 A1 * | 11/2004 | Smith et al. | 62/103 |
| 2005/0199509 A1 * | 9/2005 | Ross | 205/633 |
| 2006/0101832 A1 | 5/2006 | Wurzinger et al. | |
| 2007/0210090 A1 | 9/2007 | Sixt et al. | |

FOREIGN PATENT DOCUMENTS

| | | |
|---|---|---|
| DE | 10 2004 055 148 | 5/2006 |
| DE | 20 2006 004344 | 7/2006 |
| WO | 02/28741 | 4/2002 |
| WO | 2005/066559 | 7/2005 |

\* cited by examiner

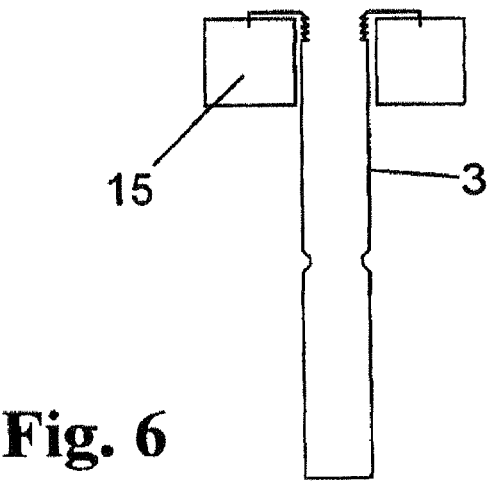
Fig. 6
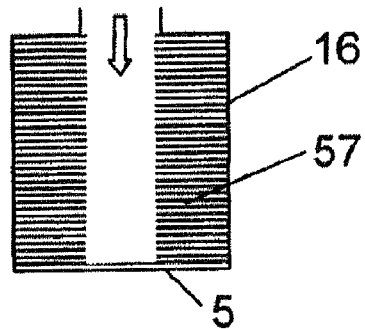
Fig. 7
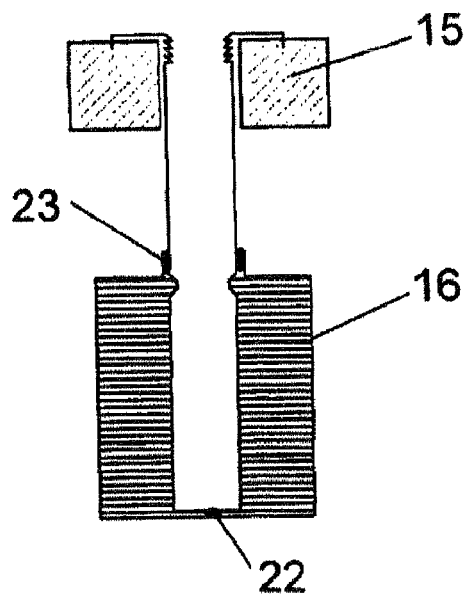

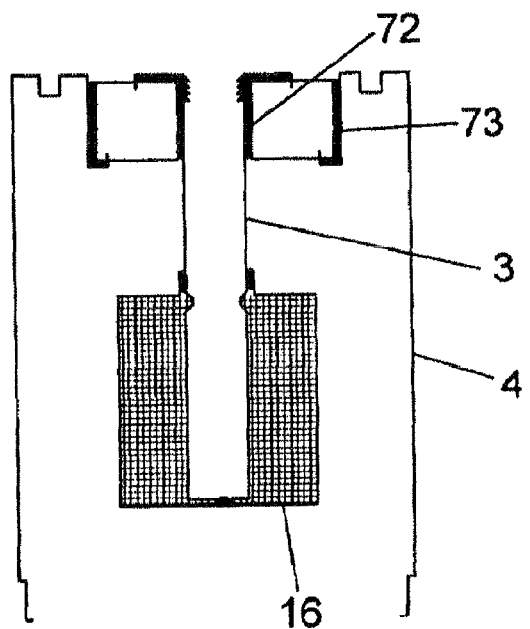
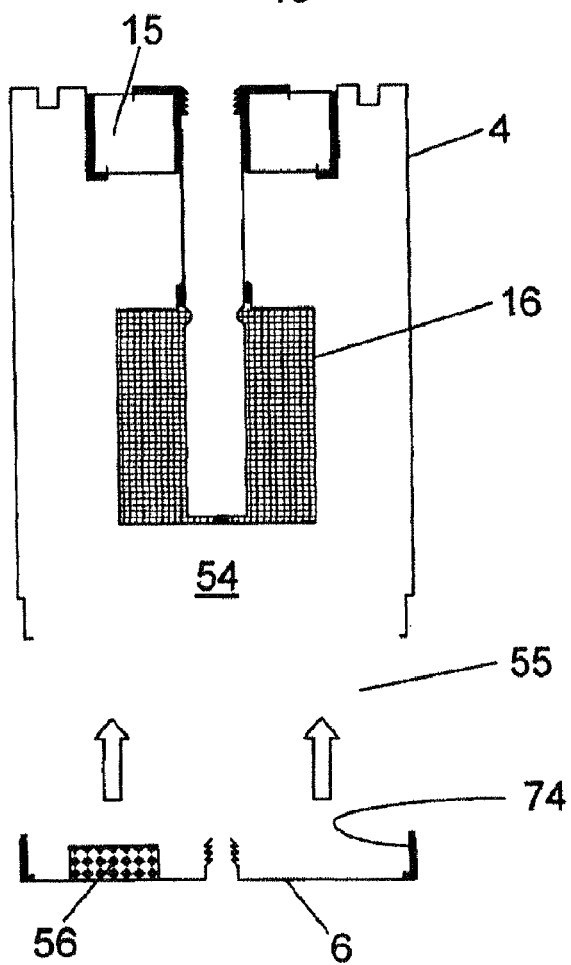

TRANSPORT CONTAINER FOR MAINTAINING THE TEMPERATURE OF FROZEN GOODS

CROSS-REFERENCE TO A RELATED APPLICATION

This U.S. patent application contains some subject matter which is similar to some subject matter of U.S. patent application Ser. No. 10/585,378, filed on Apr. 6, 2007.

BACKGROUND OF THE INVENTION

The invention relates to a transport container for maintaining the temperature of frozen goods, in particular frozen biological tissue samples or cell cultures.

Clinical diagnostics and research often require quick analysis of tissue samples in external specialist laboratories in order to obtain results for a decision regarding therapy. The analysis methods used (e.g. RNA analyses, protein markers) are rapidly developing. Deep freezing a sample has proven to destroy the least amount of information contained therein. Since research leads to the discovery of new markers on an almost daily basis, conserving the information is important, and it makes sense not only to subject the sample to the currently available examinations but also to conserve the samples as permanently as possible by deep freezing. Should the patient develop a problem in the months or even years after the sample was taken, e.g. suffer a relapse and require therapy, renewed examination of the original sample using analysis methods which may still have been unknown when the sample was taken could be of assistance and could indicate a promising targeted, expensive modern therapy in place of an untargeted standard therapy, and justify this financially to the benefactors.

Hence, it is important to have a transport container for sending frozen individual samples and which reliably avoids a transport-dependent break of the closed freezing chain while having a design which is as small and light as possible, which satisfies existing regulations, and keeps the sending costs low. Although the complexity and costs of sending can be reduced to a certain extent by collecting samples and sending them together, with a collection period of at most five days being feasible, this does however lead to administrative and logistical complexities, with intermediate storage of the samples at very low temperatures becoming necessary. Only a very small number of hospitals have a chest freezer required for this purpose, which can cool down to −70° C. for example.

WO 2005/066 559 A2 has already disclosed a transport container for maintaining the temperature of frozen biological tissue samples and cell cultures. It comprises an insulation container which is accessible via an insulating cover part and has superinsulation with a thermal conductivity $\lambda \leq 0.002$ W/(mK). A cooling container comprising a coolant chamber is provided in the insulation container, which coolant chamber surrounds a sample chamber for the frozen goods except for an access opening on the fastener side; the coolant chamber is permanently hermetically sealed, and comprises a coolant which emits the cold by solid/liquid phase transition. The coolant undergoes phase transition in the temperature range between −15° and −100° C., in particular between −30° and −85° C. and has a heat of fusion of at least 50 J/ml.

The cooling container with the coolant chamber and the sample chamber can be removed from the insulation container in this known transport container. The sample chamber extends almost to the upper end of the cooling container. The metallic inner wall of the insulation container merges into the outer wall and there is metallic contact between them.

This known embodiment already affords the possibility of maintaining the temperature of frozen samples for a number of days by using a coolant with a high heat of fusion and by means of the superinsulation with low thermal conductivity; however, the prescribed stringent requirements cannot always be reliably fulfilled because thermal bridges are present, as a result of which the coolant can be exhausted prematurely due to the detrimental influx of heat, and hence this can lead to a loss of information in the sample. Moreover, it was found that the handling of the known transport container is not yet ideal.

SUMMARY OF THE INVENTION

Accordingly, the invention is based on the object of developing a transport container which is improved with regard to its functionality and handling, ensures a reliable deep-frozen state during storage and transport, completely satisfies the existing transport regulations for frozen biological material, and can be produced without problems.

Using the known transport container described above as a starting point, according to the invention, this object is achieved by virtue of the fact that the cooling container comprising the coolant chamber is fixedly integrated in the insulation container; that the insulation container extends beyond the sample chamber by a length which exceeds its transverse dimensions by at least a factor of three by forming a neck-shaped opening; that on the outer end of the neck opening, provision is made for an insulation ring, which insulates the inner wall and the outer wall of the insulation container from each other, and elastically mounts the inner wall with the connected cooling container with respect to the outer wall, a plug being assigned to the cover part and which extends into the neck opening with an insulation shaft, fills the neck opening substantially over its entire length, and is sealed from the inner wall of the insulation container on the protruding end by means of a neck seal; and that a container seal is arranged between the insulation container and the cover part, an evacuation apparatus being provided for evacuating the cover interior, including the neck opening gap surrounding the insulation shaft.

Thermal bridges in the region of the access to the sample chamber can be reliably avoided by means of these measures so that a particularly good performance with a long-lasting cooling effect can be achieved. A thermally conducting, metallic connection between the inner wall and the outer wall of the insulation container is avoided by means of the insulation ring, with an influx of heat into the sample chamber through the inner wall being further reduced by means of the long neck opening. Additionally, despite the weight of the cooling container with the coolant hanging on the inner wall, the latter can be designed to be thin due to its elastic mounting, and hence the conduction cross section can be further reduced. Integrating the cooling container furthermore makes a relatively narrow neck opening possible, which likewise reduces the heat conducting inner wall cross section. In addition, heat input due to convection of the air in the cover interior and within the adjacent neck opening is counteracted by only a narrow neck opening gap remaining as a result of the plug with the insulation shaft and, moreover, it being possible to evacuate the trapped quantity of air.

If the entire insulation container were to be produced from plastics with low thermal conductivity to avoid the thermal bridge between inner wall and outer wall of the insulation container, this would have the disadvantage that said plastic has to be not only resistant against the (organic) coolant, but additionally has to be stable at very low temperatures and highly vacuum-tight. This also means that neither organic degassing of the plastic itself, nor diffusion of the coolant is permitted. This dilemma cannot be solved by installing a separate coolant container made of metal into the plastic container either, because in that case a gap is created between the sample chamber and the neck which is no longer accessible in everyday use. However, due to existing transport regulations for biological samples and tissue samples, and for reasons of hygiene, the sample space must be self-contained and easy to clean should the transport container be reused. For this reason, it is expedient to fixedly integrate the cooling container into the insulation container and to make the wall of the sample chamber and the neck opening, together with the inner wall of the cooling container, from one piece, for example from stainless steel, and thus obtain a seamless sample chamber. In this case, the metallic inner wall additionally has the advantage of an improved heat transfer during the cold-loading prior to the use of the container, that is to say during the transition of the liquid coolant into the solid phase.

The transport container according to the invention permits a cooling duration of approximately 14 days after cold-loading with complete transition of the coolant into the solid state, and hence permits cold-loading by the supplier, and a "ready to use" system, in which the customer, e.g. a hospital, is supplied with ready-for-use transport containers, which are sent to the customer by the supplier with the required reliability, can be intermediately stored by the customer for up to a week, and can then be sent to a central laboratory by the customer.

Expedient refinements and developments of the invention emerge from the dependent claims. These also relate to expedient measures in conjunction with the cold-loading, and will be addressed in the following description of the figures.

The transport container according to the invention and its production, as well as cold transfer devices assigned to the transport container for cold-loading are described in more detail below in an exemplary manner on the basis of schematic drawings, in which:

BRIEF DESCRIPTION OF THE DRAWINGS

FIGS. 4 to 7 show, in vertical sections, production steps during the assembly of the cooling container and its connection to the inner wall of the insulation container;

FIG. 8a shows a detail enlargement from FIG. 8 after the filling opening has been hermetically sealed;

FIGS. 9 to 12 show, in vertical sections, the further assembly of the insulation container while integrating the cooling container;

FIG. 14 shows, in an enlarged scale and partly in a vertical section, the plug, provided in accordance with FIG. 1, which is installed into the neck opening before the cover part is put on;

DESCRIPTION OF THE PREFERRED EMBODIMENTS

Figure 1:
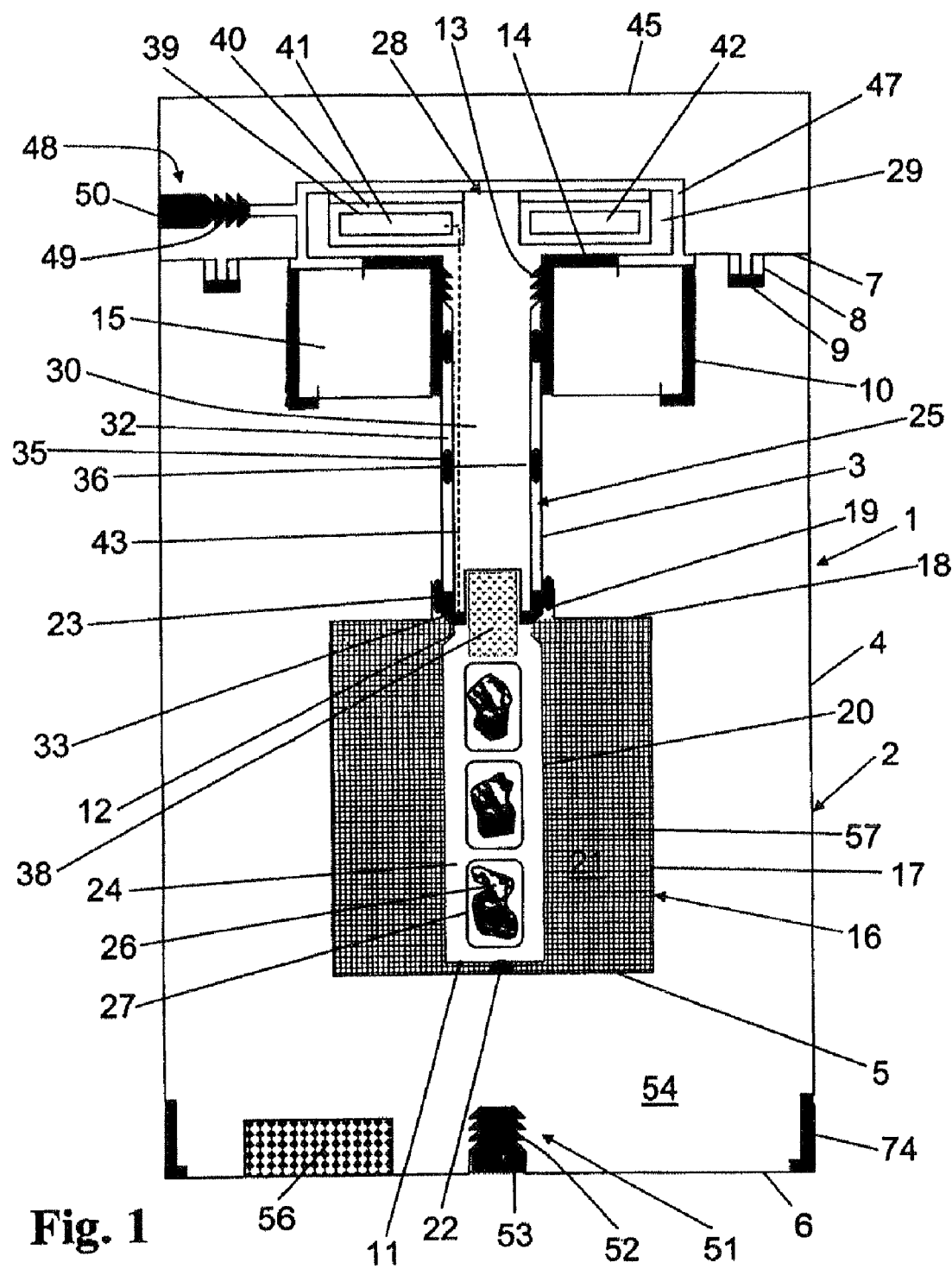
FIG. 1 shows a section through the container axis of a transport container with three samples.

The transport container 1, drawn in an upright position in FIG. 1, comprises an approximately cup-shaped insulation container 2 with an inner wall 3 and an outer wall 4, as well as an inner base 5 and an outer base 6. The outer base 6 (as is also explained in FIG. 11) is plugged onto the slightly retracted lower end of the outer wall 4 and adhesively bonded or soldered onto the latter.

At the upper end, the outer wall merges into an interior flange 7, which comprises an annular groove 8 for holding a container seal 9 and which merges into a downwardly extending, peripheral connection web 10.

The inner wall 3, produced from thin-walled stainless steel, is designed to be thin like a pipe and is provided at its lower end with a chamber base 11; it has a beaded constriction 12 at medium height, supports a female thread 13 at its upper end, and merges directly above this into an outwardly protruding annular flange 14.

An insulation ring 15 is provided at the upper end of the insulation container 2, by means of which ring the annular flange 14 of the inner wall 3 and the connection web 10 of the outer wall 4 are fixedly adhesively bonded to one another at a distance, as can be seen in FIGS. 10 and 11 as well. In this fashion there is a stretch of insulation between the metallic walls 3 and 4 of the insulation container 2. The insulation ring 15, adhesively bonded in-between, at the same time effects an elastic mounting of the inner wall 3 with respect to the outer wall 4 in the manner of a silent block.

An annular cooling container 16 is fixedly integrated into the insulation container 2 and it has a peripheral wall 17, which merges at its upper end into a cover flange 18 with an upwardly extending inner web 19. The cooling container 16 is integrated into the insulation container in such a way that the former's inner peripheral wall 20 is formed by the lower half of the inner wall 3, while the inner base 5 and the chamber base 11 form the flat central region of the coolant chamber 21. A central weld spot 22 between the inner base 5 and the chamber base 11 reduces possible mechanical loads in the upper region of the inner wall 3. The inner web 18 of the cooling container 16 is fixedly connected to the inner wall 3 by means of a welding bead 23, and as a result of this the coolant chamber 21 is hermetically sealed.

Figure 5:
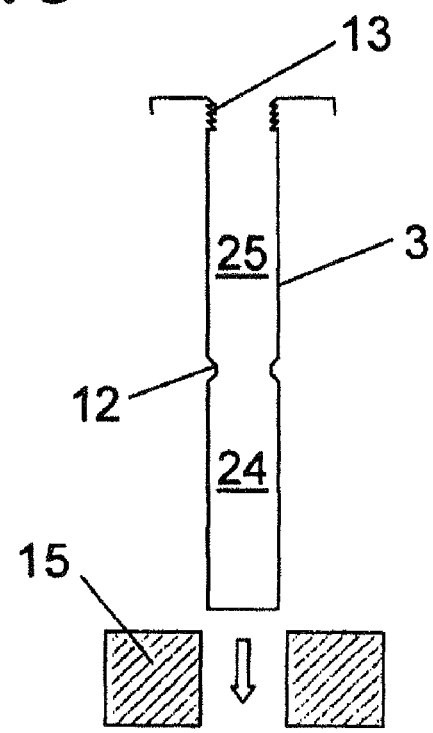

The constriction 12 of the inner wall 3 subdivides the space within the inner wall 3 into a lower sample chamber 24 and an upper neck opening 25 (FIG. 5). The sample chamber 24 can, as illustrated, simultaneously hold three different samples 26 in respectively one sample container 27, which samples can be Nunk tubes, for example.

Figure 14:
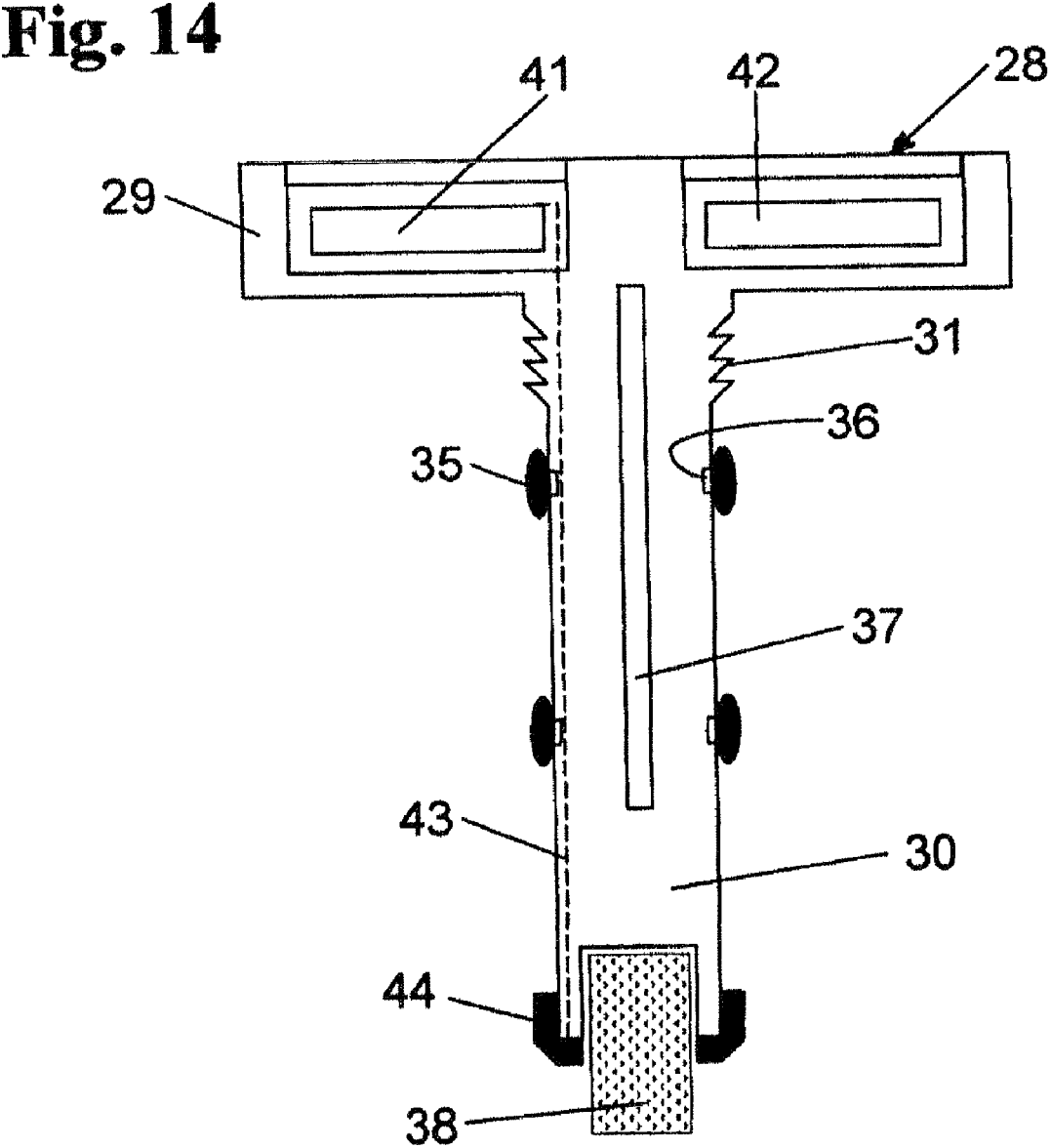

A plug 28 is installed in the neck opening 25, which is illustrated in an enlarged form in FIG. 14. In the vertical section, the plug 28 is T-shaped with an upper head 29 having an increased width and a central insulating shaft 30, which extends downward and has a male thread 31 on its upper end. By means of this, the plug 28 is screwed into the female thread 13 of the inner wall 3. In this case, the length of the insulation shaft 30 corresponds to the height of the neck opening 25 so that only an annular gap 32 of the latter remains free. On its lower end, the insulation shaft 30 carries an annular neck seal 33, which, when the plug 28 is screwed in, is pushed against the valve seat 34 (FIG. 20) which is formed by the constriction 12 on the inner side of the inner wall 3, and thus seals the sample chamber 24 with respect to the neck opening 25 or the annular gap 32. This annular gap 32 is subdivided into sections by O-rings 35 which are inserted into annular grooves 36 of the insulation shaft 30. This counteracts heat transmission through the annular gap 32 due to convection. A longitudinal groove 37 (FIG. 14) in the insulation shaft 30 extends beyond the O-rings 35 and the male thread 31, and ensures pressure balance between the gap sections and the upper side of the plug 28.

The insulation shaft 30 carries a protruding pad 38 on its underside, which pad 38 is used to absorb sample liquids, which may be leaking, and can easily be replaced. Cavities 39 are provided in the head 29 which are accessible from above and covered by cavity covers 40. By way of example, the cavities 39 can accommodate a data logger 41 and a battery 42 associated with it. The data logger 41 is connected to a temperature sensor 44 at the lower end of the insulation shaft 30 via a signal line 43, which is molded-in in a vacuum-tight fashion, so that the temperature prevailing in the sample chamber 24 can be continuously recorded. As an alternative, provision can be made for a simplified plug without data logger, battery and temperature sensor.

The insulation container 2 is covered by a heat-insulating cover part 45, on whose underside provision is made for an annular web 46 which interacts with the container seal 9 in a sealing fashion. On its underside, the cover part 45 has a recess which forms the cover interior 47. This loosely holds the head 29 of the plug 28.

An evacuation apparatus 48 is provided in the cover part 45, which evacuation apparatus 48 is adjacent to the cover interior 47 and is in the form of an evacuating valve 49 with a fitted protective cap 50.

A corresponding evacuation apparatus 51 with an evacuation valve 52 and a protective cap 53 is installed in the outer base 6 of the insulation container 2. As a result of this, it is possible for the insulation chamber 54, which is formed in the insulation container 2 and completely filled with a vacuum-supporting material 55, such as pyrogenic silicic acid for example. This effects a stiffening of the structure when the insulation chamber is evacuated. A getter 56 is installed in the base area of the insulation container 2 in order to bind residual gases in the insulation chamber 54.

Provision is also made in the coolant chamber 21 for a metal wool filling 57 in addition to the coolant filling; as a result of this, thermal conduction within the coolant chamber is markedly improved and this assists the cold-loading and the liquid/solid phase transition of the coolant.

Figure 2:
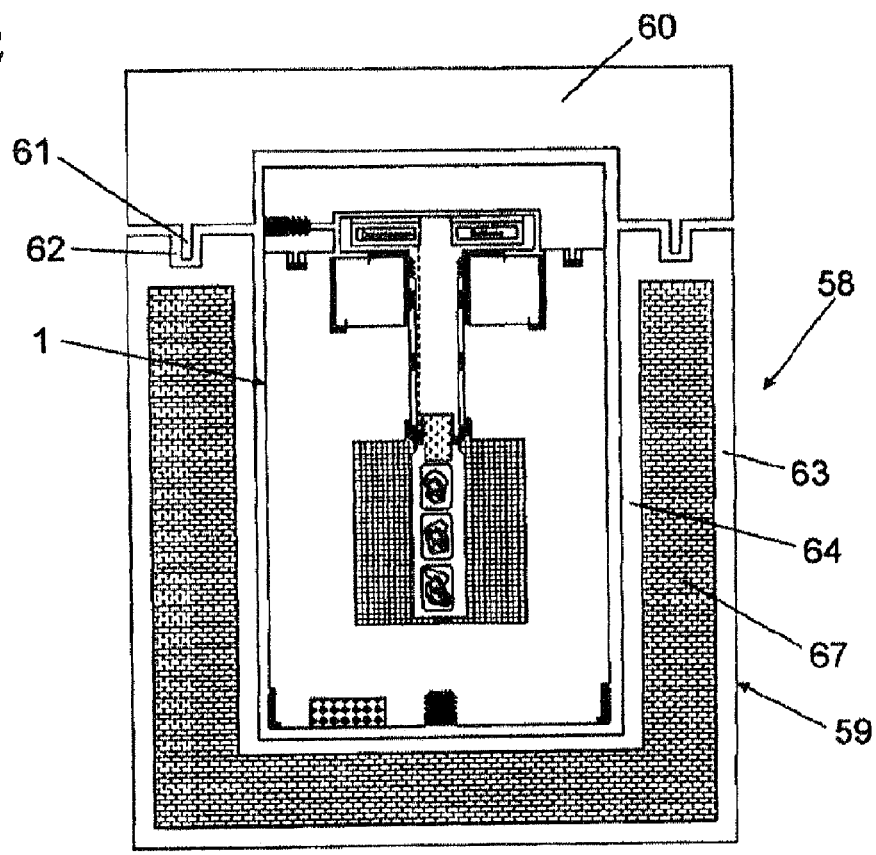
FIG. 2 shows the transport container in accordance with FIG. 1, with an outer container serving as an outer packaging, in a reduced scale and also in a sectional view.
Figure 3:
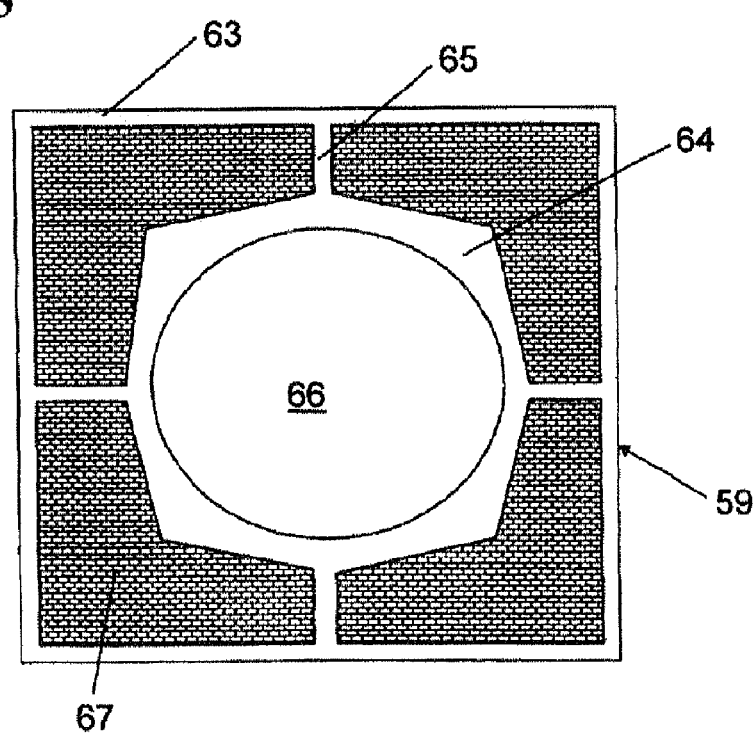
FIG. 3 shows a further-reduced cross section of the outer container in accordance with FIG. 2.

Optionally employed surrounding packaging 58 for the transport container 1 is shown in a vertical and a horizontal section in FIGS. 2 and 3, respectively. This surrounding packaging 58 comprises an outer container 59 with an outer cover 60, which, by means of a peripheral sealing web 61, meshes into a corresponding sealing groove 62 in the upper edge of the outer container 59. The outer container 59 and the outer cover 60 are made from insulating material and have a quadratic outer cross section and a circular inner cross section.

The outer container 59 is produced as hollow body with an outer wall 63 and an inner wall 64, with connection webs 65 extending between them. Together with the outer cover 60, the inner wall 64 surrounds a cylindrical reception chamber 66 which is matched to the transport container 1.

The cavity formed between the outer wall 63 and the inner wall 64 is also filled with a coolant 67, which undergoes a solid/liquid phase transition in a comparatively high temperature range between C and −15° C. It can be water or saline. The surrounding packaging 58 and, in particular, the coolant 67, which is frozen before use, form a barrier against the influx of heat into the surrounded transport container 1.

FIGS. 4 to 13 illustrate the individual components which form the transport container 1 and how the latter is expediently assembled.

Figure 4:
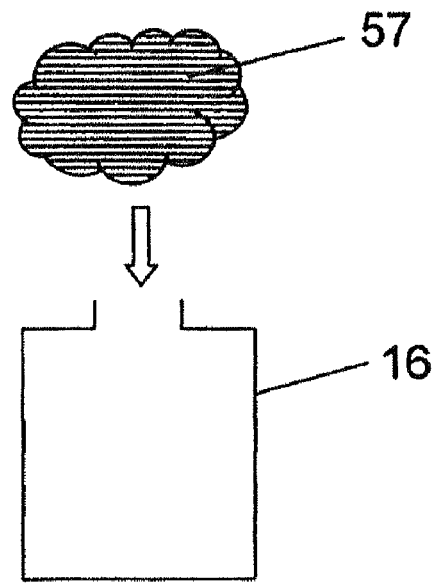

In accordance with FIG. 4, the cooling container 16 is provided with the metal wool filling 57, the latter expediently being a tangled-up metal thread of copper, for example. This metal wool filling 57 is arranged in a substantially annular fashion in the cooling container 16, as is made clear in FIG. 6, with a thin metal wool layer or at least one thread section remaining centrally above the base 5 of the cooling container 16.

In accordance with FIG. 5, the inner wall 3, with the female thread 13 and the constriction 12, is pushed into the insulation ring 15; in fact, it is pushed until it is in the position shown in FIG. 6, upon which the inner wall 3 is inserted into the cooling container 16, as shown in FIG. 6, until the position shown in FIG. 7 is reached. In this position, the bases of the inner wall 3 and of the cooling container 16 are supported on each other by a weld spot 22 and the cooling container 16 is fixedly connected at its upper end to the inner wall 3 by forming the welding bead 23.

Figure 8:
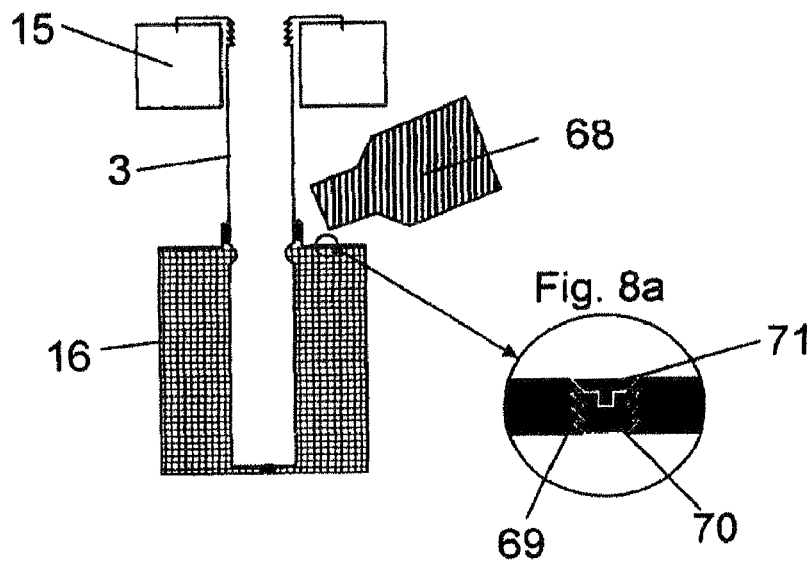
FIG. 8 shows a vertical section of filling the cooling container with the coolant through a filling opening.

The cooling container 16 has on its upper side a thread opening 69, through which, in accordance with FIG. 8, liquid coolant is poured into the former from a vessel 68, until the cooling container 16 is substantially completely filled. This coolant is an organic substance with a solid/liquid phase transition temperature in the temperature range between −15° and −100° C., and preferably between −30° and −85° C., and has a heat of fusion of at least 50 J/ml. Such coolants can be, for example, octane 1-hexanol, 2-hexanone, hexanal, pyridine, 1,2,4-trimethylbenzene, 1,3,5-trimethylbenzene or chlorobenzene.

After the filling, the thread opening 69 of the cooling container 16 is permanently hermetically sealed by virtue of the fact that, in accordance with FIG. 8a, a set screw 70 is firstly screwed in; the remainder of the opening remaining is then weld shut and subsequently the solder material 71 which is protruding is removed so as to be flush.

Figure 9:
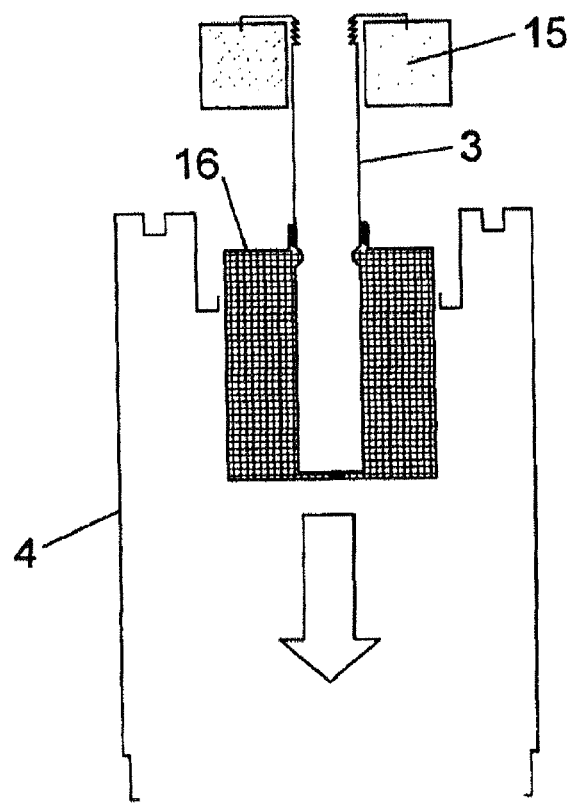

Now, in accordance with FIG. 9, the arrangement comprising the cooling container 16, the inner wall 3, and the insulating ring 15 is inserted into the outer wall 4 until it reaches the position in accordance with FIG. 10. In this position, the inner wall 3 and the outer wall 4 are connected in a vacuum-tight fashion to the insulating ring 15 by means of adhesive layers 72 and 73, with the elastic mounting of the arrangement comprising cooling container 16 and inner wall 3 with respect to the outer wall 4 being achieved at the same time.

Figure 12:
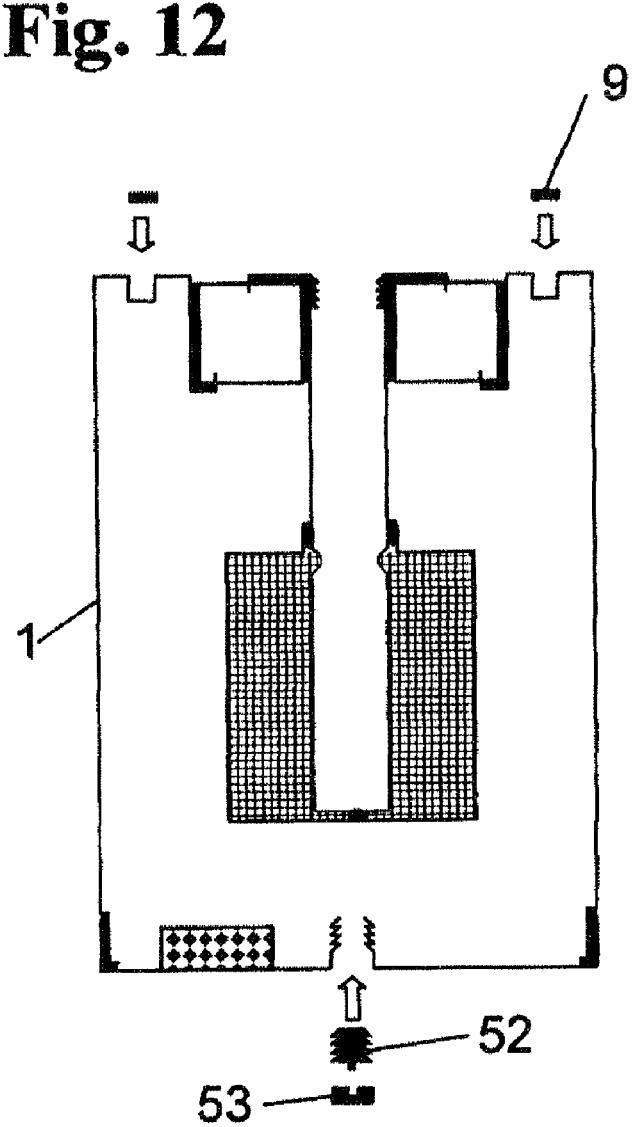
Figure 13:
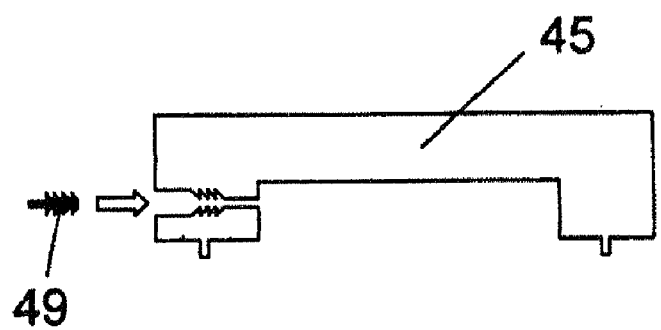
FIG. 13 shows, in a vertical section, the cover part of the insulation container with indicated installation of an evacuation valve.

Subsequently, in accordance with FIG. 11, the insulation chamber 54 of the insulation container 2 formed within the outer wall 4 is filled with the vacuum-supporting material 55, and the outer base 6 with the getter 56 is pushed onto the lower end of the outer wall 4 and connected in a vacuum-tight fashion to the outer wall 4 by means of an adhesive 74, so that the arrangement shown in FIG. 12 is obtained into which the container seal 9 is subsequently inserted at the upper end, and the evacuation valve 52 with the protective cap 53 is screwed in at the lower end in a vacuum-tight fashion, upon which the insulation container 2 is evacuated. In accordance with FIG. 13, the evacuation valve 49 is also screwed into the cover part 45 in a vacuum-tight fashion.

Finally, the plug 28 is completed in accordance with FIG. 14 by installing the data logger 41, the battery 42 and the temperature sensor 44 in it, and by attaching the O-rings 35 and the pad 38.

The cold-loading of the transport container 1, that is to say the phase transition of the coolant in the cooling container 16 from the liquid phase into the solid phase, can be effected in different ways and with the aid of differing devices which are explained in FIGS. 15 to 19.

Figure 15:
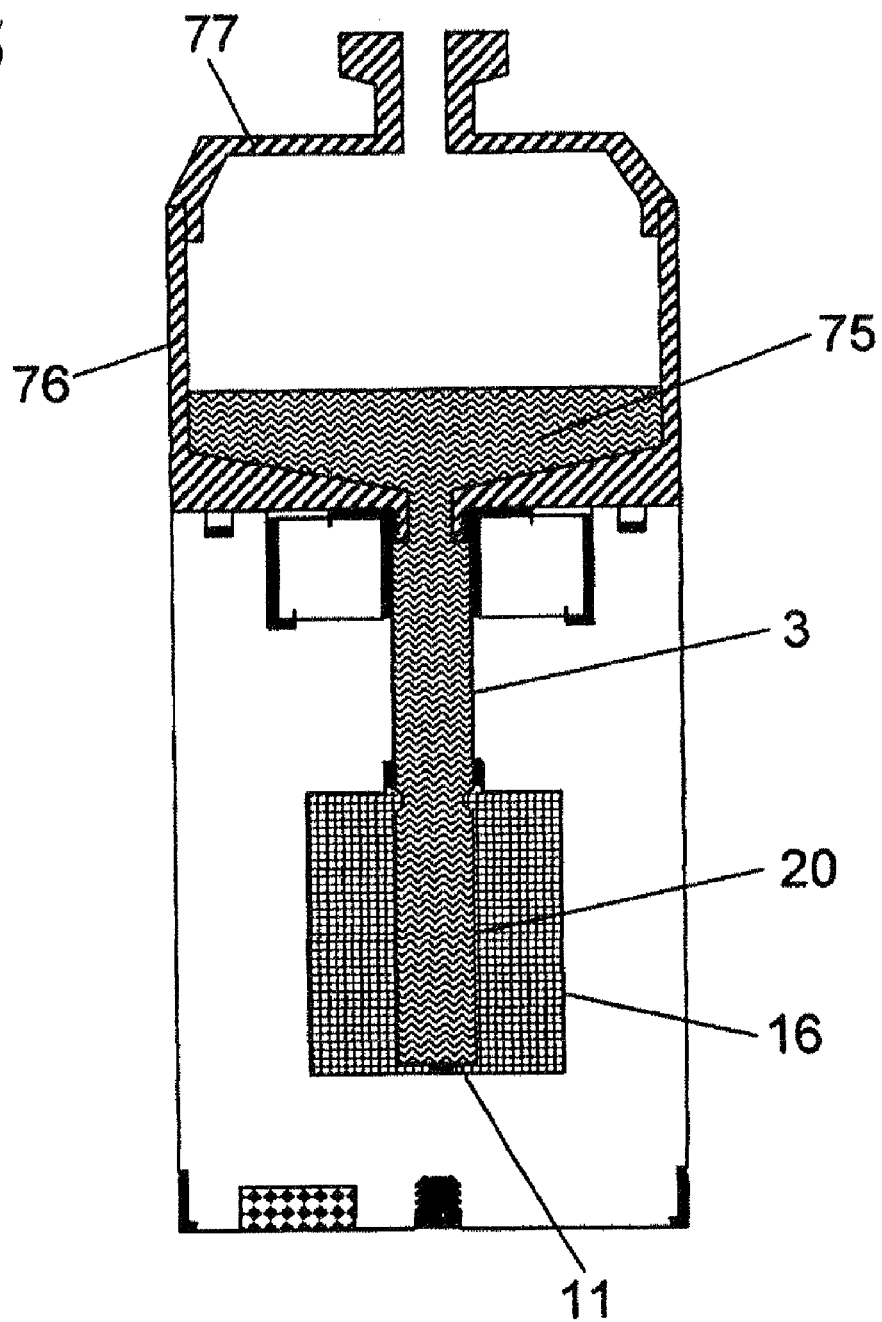
FIG. 15 shows, in a vertical section, the direct cold-loading of the transport container with liquid nitrogen.

FIG. 15 shows direct cold-loading with, for example, liquid nitrogen 75, for the purposes of which a filling-funnel 76 is screwed into the female thread 13 of the open transport container 1 (without cover part 45 and plug 28) and provided with an open cover 77 during cold-loading. The filling-funnel 76 and cover 77 are produced from an insulating material. The advantage of this direct cold-loading is that the entire lower half of the inner wall 3, including the inner peripheral wall 20 and the chamber floor 11, is contacted by liquid nitrogen 75, and hence active in transferring the cold, which is in the interests of a short loading time. However, extra care has to be taken that no (liquid) nitrogen remains in the sample chamber 24 and the neck opening 25 after the cold-loading has been completed.

Figure 16:
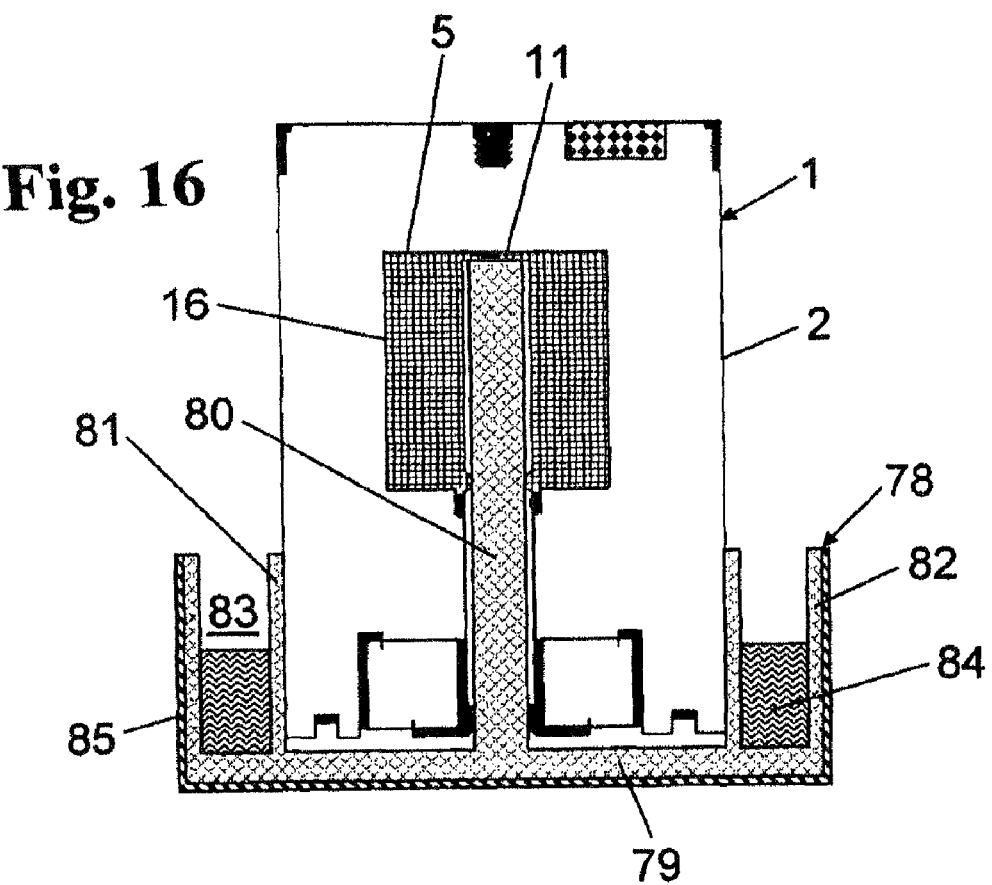
FIG. 16 shows a cold-loading apparatus for indirect cold-loading of the transport container with liquid nitrogen using an upwardly extending cooling finger.

In accordance with FIG. 16, provision is made for indirect cold-loading by means of liquid nitrogen (or else dry ice, or a dry ice/liquid mixture, such as isopropanol). A bowl-shaped cold transfer device 78 with a base plate 79, from which a central long cooling finger 80 as well as an inner peripheral wall 81 and an outer peripheral wall 82 extend upward, is used for this purpose. An annular chamber 83 for the liquid nitrogen 84 is formed between the two peripheral walls 81 and 82. The cold transfer device 78 is provided with an outer insulation 85 which surrounds the base plate 79 and the outer peripheral wall 82. The base plate 79, the peripheral walls 81 and 82, and the cooling finger 80 are preferably produced in one piece from a material with a high thermal conductivity, such as copper.

For the purposes of cold-loading, the inner wall 3 of the transport container 1 is plugged onto the cooling finger 80 while the cover-free transport container 1 is an inverted position, the cooling finger being slightly longer than the wall, with the weight of the container ensuring good contact between the upper end face of the cooling finger 80 and the chamber floor 11. In this case, the diameter of the inner peripheral wall 81 is dimensioned such that, as illustrated, it holds the lower end of the transport container 1 which is in the loading position.

In the case of loading in accordance with FIG. 16, the cold or heat is transported through the base plate 79 and the cooling finger 80 and, substantially, through the chamber floor 11. The heat exchange with the coolant in the cooling container 16 is mainly carried out by the metal wool filling, which also extends between the chamber base 11 and the inner base 5, and which substantially shortens the cold-loading time in view of the poor thermal conductivity properties of organic coolants. This is also assisted by the fact that the heat is transmitted through the chamber base 11 at the highest point of the coolant, which sinks downward during cooling, and thus improves the overall freezing of the coolant.

Figure 17:
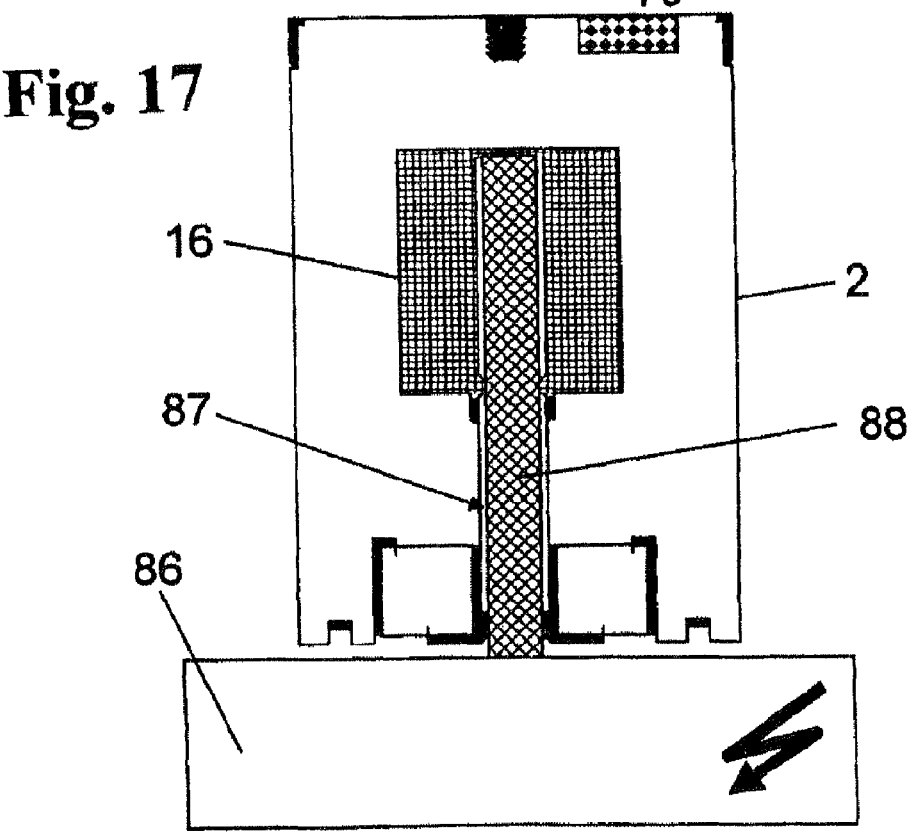
FIG. 17 shows the cold-loading by means of a cooling finger by using a different cold source.

In accordance with FIG. 17, provision is made for indirect cold-loading, which corresponds to the cold-loading in accordance with FIG. 16, by means of an active cooler 86 as a source of cold, e.g. a Stirling cooler. From this, a correspondingly long metallic cooling finger 87, made from a material with a high thermal conductivity such as copper, again extends upward.

Figure 18:
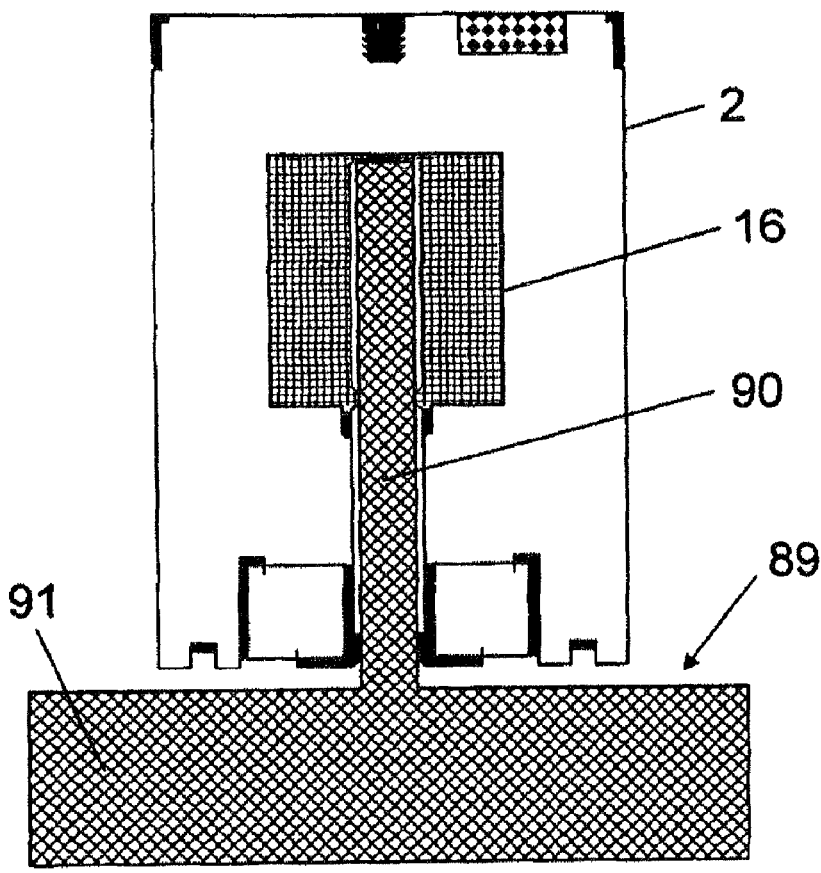
FIG. 18 shows a cold transfer device with an upwardly extending cooling finger to be arranged in a freezer room.
Figure 19:
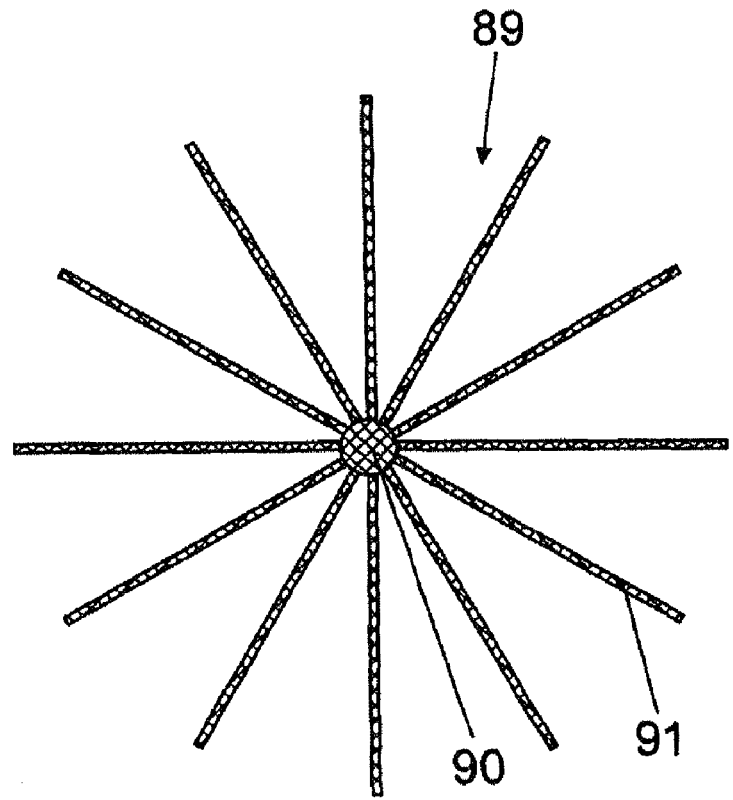
FIG. 19 shows a plan view of the cold transfer device in accordance with FIG. 19 comprising lamellae and an upwardly extending cooling finger.

In accordance with FIGS. 18 and 19, provision is again made for indirect cold-loading; however, in this case, it is made for passive cooling which is effected by insertion into a freezer room. For this purpose, a cold transfer device 89 is provided which in turn has an upwardly extending cooling finger 90 which is connected at its lower end to lamellae 91 which are arranged in a star shape, as shown in FIG. 19. In this case too, the cooling finger 90 and the lamellae 91 are composed of a metal with a high thermal conductivity, such as copper.

Figure 20:
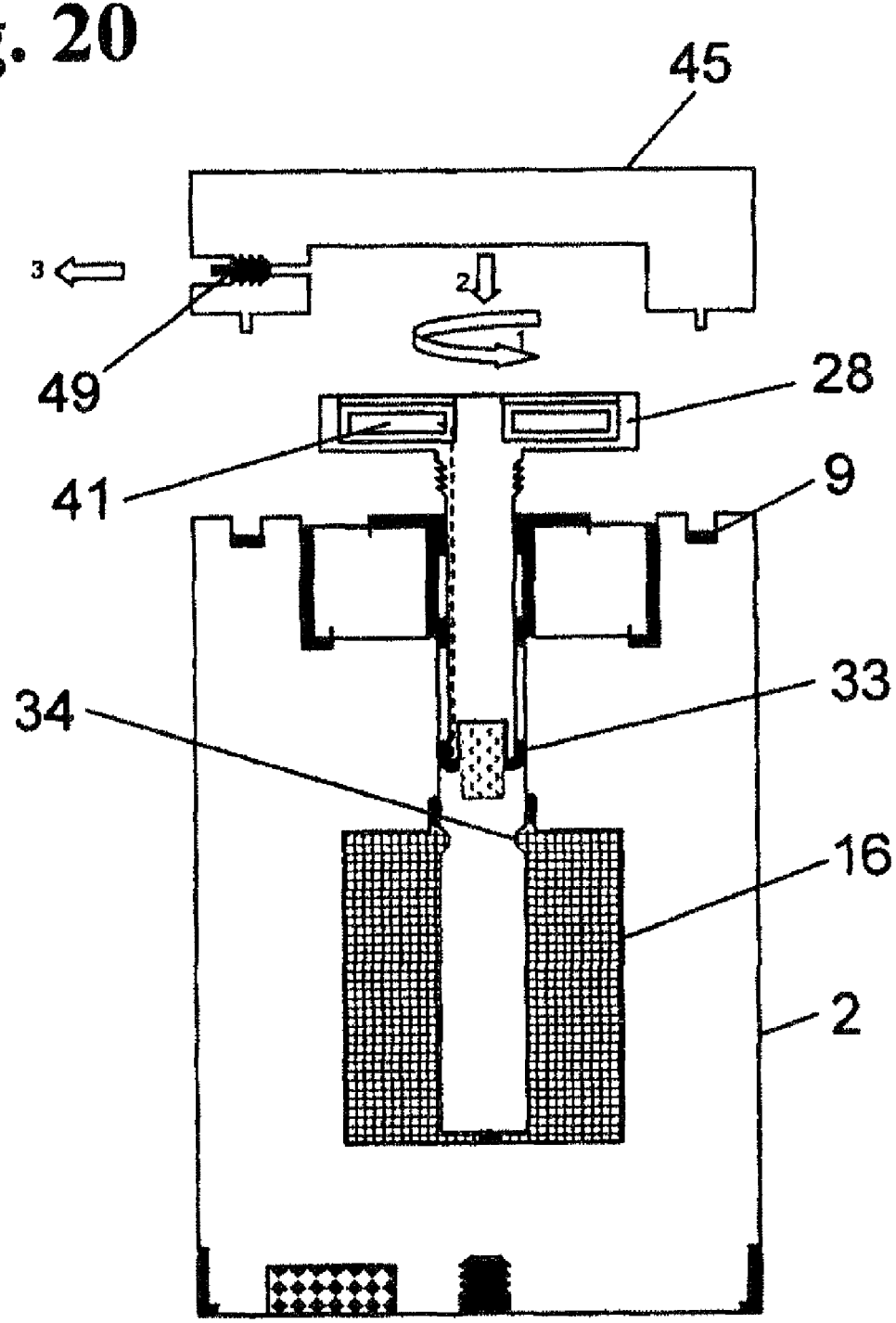
FIG. 20 shows, in a vertical section, the assembly of the transport container ready to be sent after cold-loading.

FIG. 20 illustrates the assembly of the transport container 1 ready to be sent, in which the plug 28 has been inserted and screwed-in in accordance with arrow 1, until its neck seal 33 is pressed against the valve seat 34 in a sealing fashion. In accordance with arrow 2, the cover part 45 is then put on, whereupon, in accordance with arrow 3, the cover interior 47 is evacuated by means of the evacuation valve 49. The external excess pressure effected in this fashion ensures that the cover part 45 pushes on the insulation container 2 in the axial direction while it is securely sealed by means of the container seal 9. At the same time, heat transfer by convection in the annular gap 32 is suppressed.

The cooling container 16 with the frozen coolant is then screened from the influx of heat by the superinsulation formed by the evacuated insulation container 2, and by the plug 28 with its insulation shaft 30, and by the evacuated annular gap 32 around the insulation shaft 30, so that the frozen state or the cold-loading is maintained as far as possible, even in the surrounding temperature while being sent to the site of operation (hospital).

Figure 21:
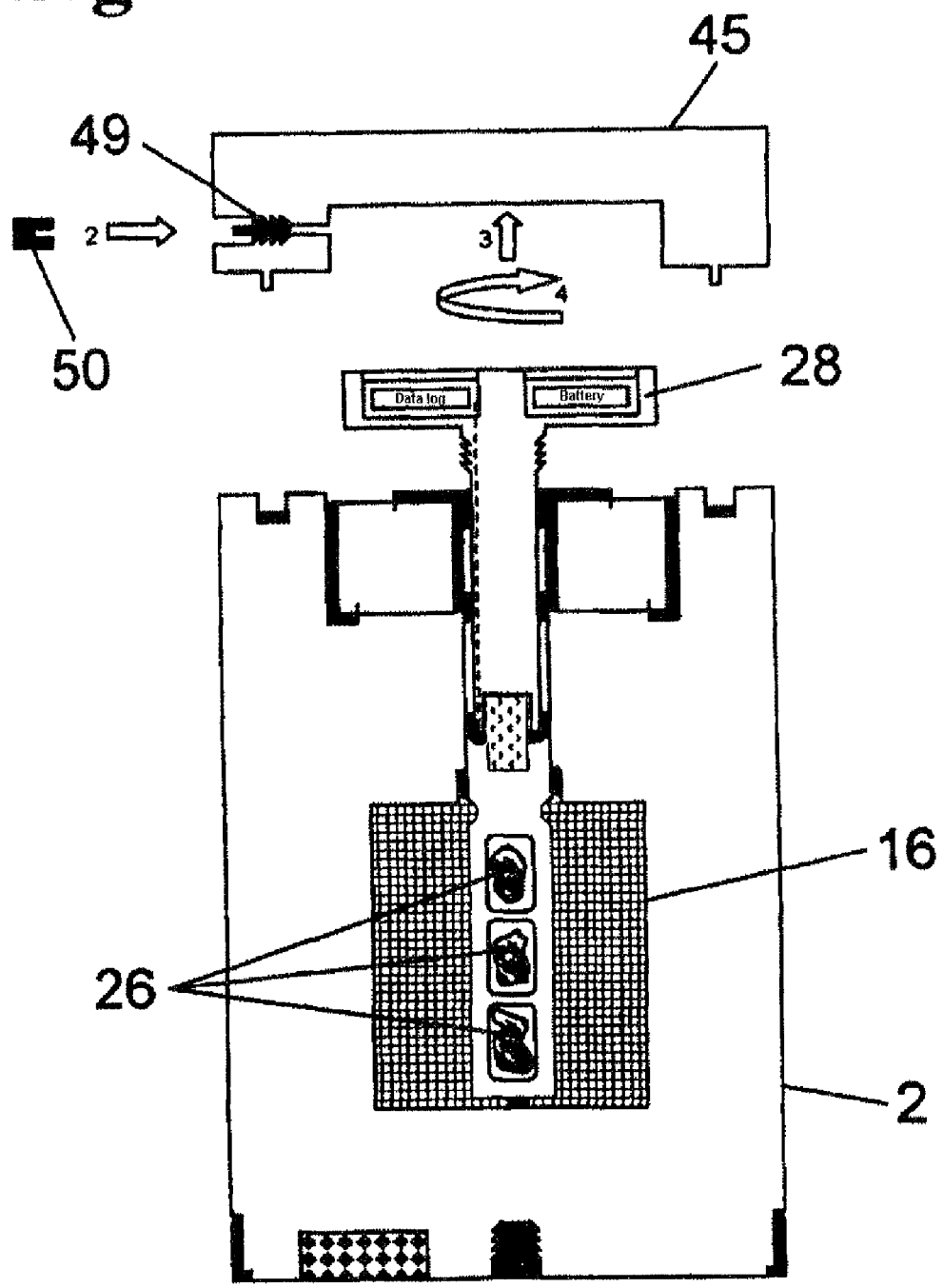
FIG. 21 shows the opening, filling and resealing of the transport container at a decentralized location where the samples accumulate.

FIG. 21 illustrates the use at the site of operation. The protective cap 50 is removed, the cover interior 47 is ventilated by actuating the evacuation valve 49, the cover part 45 is removed and the plug 28 is unscrewed and removed in accordance with the steps in indicated by arrows 1 to 4; after this, the frozen samples 26 in the sample containers 27 are inserted into the sample chamber 24. Subsequently, the transport container 1 is sealed again as soon as possible in reverse order, specifically by screwing in the plug 28, putting on the cover part 45, evacuating the cover interior 47 and putting on the protective cap 50. This results in the state illustrated in FIG. 1. Now the samples 26, which are protected from heating up by the above-described insulating effect of the transport container 1 and in particular the cold capacity of the frozen coolant in the cooling container 16, can be sent to their destination. If necessary, this is also possible without using the surrounding packaging 58 in accordance with FIGS. 2 and 3. The surrounding packaging 59 is used in particular in the case of long storage periods and/or transport periods, and in the case of relatively high surrounding temperatures.

At the destination, the samples 26 are then removed from the transport container 1, analyzed and possibly permanently stored in a freezer room. The data logger 41 is used to check that the envisaged storage temperature in the sample chamber 24 was maintained and the samples 26 were correspondingly not damaged.

Provision is made for the transport container 1 to be reused; to do this only requires renewed cold-loading and the previously described assembly, and sending it to the site of operation. Moreover, it is suggested to check and renew the evacuation of the insulation container 2 after empirically defined time intervals.

In summary, the transport container according to the invention can be described as follows: the transport container 1 comprises superinsulation in the form of an evacuated insulation container 2 with a vacuum-supporting material 55. A cooling container 16 is integrated therein, which contains a thermally-conducting metal wool filling 57 and which is filled with an organic coolant which undergoes a solid/liquid phase transition in the temperature range between −30° and −85° C. and which has a heat of fusion of at least 50 J/ml. Provision is made for a thin, cylindrical sample chamber 24 for holding deep frozen tissue samples 26, which chamber is surrounded by the cooling container 16 and integrally merges into a long neck opening 25, which in turn is substantially filled by the insulating shaft 30 of a plug 28, which can be screwed in, and sealed with respect to the sample chamber 24. The annular gap 32 which then remains can be evacuated by means of an evacuation apparatus 48. The plug 28 is provided with a pad 38, extending into the sample chamber 24, and a data logger 41 for recording the temperature in the sample chamber 24. After the coolant has been frozen, the transport container 1 makes transport times and intermediate storage of up to 14 days possible without any risk to the held tissue samples 26.

The invention claimed is:

1. A transport container for maintaining a temperature of frozen goods (26), comprising
   a) an insulation container (2), which
   b) is accessible via an insulating cover part (45) and
   c) has superinsulation with a thermal conductivity $\lambda \leq 0.002$ W/(mK);
   d) a cooling container (16) comprising a coolant chamber (21) arranged in the insulation container (2), which coolant chamber
   e) surrounds a sample chamber (24) for the frozen goods (26) except for an access opening (25) on a fastener side,
   f) is permanently hermetically sealed and
   g) comprises a coolant which
   h) emits cold by solid/liquid phase transition,
   i) undergoes phase transition in a temperature range between −15° and −100° C. and
   j) has a heat of fusion of at least 50 J/ml, wherein
   k) the cooling container (16) comprises a coolant chamber (21) is fixedly integrated in the insulation container (2);
   l) the insulation container (2) extends beyond the sample chamber (24) by a length which exceeds its transverse dimensions by at least a factor of three by forming a neck-shaped opening (25);
   m) on an outer end of the neck opening (25), provision is made for an insulation ring (15) which
   n) insulates an inner wall (3) and an outer wall (4) of the insulation container (2) from each other, and
   o) elastically mounts the inner wall (3) with the connected cooling container (16) with respect to the outer wall (4),
   p) a plug (28) being assigned to a cover part (45) and which
   q) extends into the neck-shaped opening (25) with an insulation shaft (30),
   r) fills the neck-shaped opening (25) substantially over its entire length, and
   s) is sealed from the inner wall (3) of the insulation container (2) on a protruding end by means of a neck seal (33);
   t) a container seal (9) is arranged between the insulation container (2) and the cover part (45), and
   u) an evacuation apparatus (48) is provided for evacuating a cover interior (47), including an annular gap (32) surrounding the insulation shaft (30).

2. The transport container as claimed in claim 1, wherein the coolant is an organic pure substance with a phase transition temperature between −30° and −85° C.

3. The transport container as claimed in claim 1, wherein the insulation container (2) is designed in a hollow-cylindrical fashion with an outer base (6) adjoining the outer wall (4), and the inner wall (3), which simultaneously forms an inner peripheral wall (20) of the cooling container (16) and defines the sample chamber (24), merges at an inner end into a chamber base (11) which is arranged in a gap distance to an inner base (5) of the insulation container (2) which forms a cooling container base.

4. The transport container as claimed in claim 1, wherein the insulation container (2) is provided with an evacuation apparatus (51) for purposes of vacuum insulation, and is filled with a vacuum-supporting material (55).

5. The transport container as claimed in claim 4, wherein the insulation container (2) is filled with powdered pyrogenic silicic acid as a vacuum-supporting material (55).

6. The transport container as claimed in claim 4, wherein a getter (56) is installed in the insulation container (2).

7. The transport container as claimed in claim 1, wherein the plug (28) comprising the insulation shaft (30) is a separate component.

8. The transport container as claimed in claim 7, wherein the plug (28) is designed as a screw plug which interacts with a female thread (13) at an outer end of the neck opening (25).

9. The transport container as claimed in claim 7, wherein the plug (28) comprises a head (29) which is widened compared to the insulation shaft (30) and which is held in a recess in the cover part (45).

10. The transport container as claimed in claim 9, wherein a head (29) of the plug (28) contains a data logger (41) and a battery (42) assigned to the latter, with the data logger (41) being connected to a temperature sensor (44) in a region of a free end of the insulation shaft (30) via a signal line (43) guided through the insulation shaft (30).

11. The transport container as claimed in claim 1, wherein the insulation shaft (30) comprises at least one annular groove (36) with an O-ring (35) for sealing it with respect to the inner wall (3) of the insulation container (2) and for subdividing the annular gap (32) between the inner wall (3) and the insulation shaft (30).

12. The transport container as claimed in claim 1, wherein on its protruding end which delimits the sample chamber (24), the plug (28) has a replaceable pad (38) for absorbing sample chamber liquids.

13. The transport container as claimed in claim 1, wherein in addition to the coolant, the coolant chamber (21) of the cooling container (16) also comprises a thermally conducting metal wool filling (57) for improved cold-loading prior to receiving the frozen goods (26).

14. The transport container as claimed in claim 1, wherein the coolant is an organic substance.

15. The transport container as claimed in claim 1, wherein the insulation container (2) and the cooling container (16) are composed of stainless steel.

16. The transport container as claimed in claim 1 wherein it is assigned surrounding packaging (58), comprising an insulating outer container (59) and an insulating outer cover (60), which surrounds a reception chamber (66) whose dimensions correspond to those of the transport container (1).

17. The transport container as claimed in claim 16, wherein the outer container (59) comprises a coolant (67) with a liquid/solid phase transition in a temperature range between 0° and −15° C.

18. The transport container as claimed in claim 1, wherein it is assigned a cold-loading apparatus which comprises a thermally highly conducting solid cooling finger (80, 88, 90), comprising copper in particular, whose length corresponds to a sum of lengths of the sample chamber (24) and neck opening (25), and whose transverse dimensions are matched to the sample chamber (24) and neck opening (25), with one end of a cooling finger (80, 88, 90) being connected to a cold transfer device (78, 87, 89).

19. The transport container as claimed in claim 18, wherein the cold transfer device (78) is a vessel (79, 81, 82) provided with outer insulation (85) for holding a low temperature coolant (84), such as liquid nitrogen or dry ice.

20. The transport container as claimed in claim 19, wherein the cooling finger (80) extends upwardly and centrally from a base (79) of the vessel (79, 81, 82) which has an outer annular chamber (83) for the coolant (84) and an inner chamber for holding the insulation container (2) which in turn is pushed onto the cooling finger (80) with a downward-pointing neck opening (25).

21. The transport container as claimed in claim 18, wherein the cold transfer device (89) is provided with lamellae (91) for increased heat transfer during cold-loading in a deep-freezer.

22. The transport container as claimed in claim 18, wherein the cooling finger is pressed against a sample chamber base (11) and dynamically tracked, so that an end side fixedly rests against the latter.

23. The transport container as claimed in claim 1, wherein it is assigned a filling-funnel (76) for direct cold-loading with a low temperature cooling medium (75), with the filling-funnel (76) being able to be screwed into a female thread (13) at an outer end of the neck opening (25).

* * * * *